United States Patent
Hanf et al.

(10) Patent No.: US 10,792,277 B2
(45) Date of Patent: Oct. 6, 2020

(54) METHODS OF TREATMENT OF FIBROSIS AND CANCERS

(71) Applicant: GENFIT, Loos (FR)

(72) Inventors: Rémy Hanf, Lille (FR); Dean Hum, Bondues (FR); Robert Walczak, Lille (FR); Benoît Noel, Loos (FR)

(73) Assignee: GENFIT, Loos (FR)

( * ) Notice: Subject to any disclaimer, the term of this patent is extended or adjusted under 35 U.S.C. 154(b) by 0 days.

(21) Appl. No.: 15/586,456

(22) Filed: May 4, 2017

(65) Prior Publication Data

US 2017/0239213 A1     Aug. 24, 2017

Related U.S. Application Data

(62) Division of application No. 14/760,880, filed as application No. PCT/EP2014/051060 on Jan. 20, 2014, now abandoned.

(30) Foreign Application Priority Data

Jan. 18, 2013   (EP) ..................................... 13305067

(51) Int. Cl.
*A61K 31/381*     (2006.01)
*A61K 31/192*     (2006.01)

(52) U.S. Cl.
CPC .......... *A61K 31/381* (2013.01); *A61K 31/192* (2013.01)

(58) Field of Classification Search
CPC ............................. A61K 31/381; A61K 31/192
See application file for complete search history.

(56) References Cited

U.S. PATENT DOCUMENTS

| | | | |
|---|---|---|---|
| 2008/0051465 A1* | 2/2008 | Tripp | .................... A61K 31/12 514/685 |
| 2011/0021637 A1 | 1/2011 | Tripp et al. | |
| 2012/0252725 A1 | 10/2012 | Darteil et al. | |
| 2015/0352065 A1 | 12/2015 | Hanf et al. | |

FOREIGN PATENT DOCUMENTS

| | | | | |
|---|---|---|---|---|
| WO | WO 2011/064350 | 6/2011 | | |
| WO | WO-2011064350 A1 * | 6/2011 | ........... | A61K 31/155 |
| WO | WO 2011/116963 | 9/2011 | | |

OTHER PUBLICATIONS

Chaudhary et al, Eur Respir J, 29, 976-985 (Year: 2007).*
Bonner, Cytokine & Growth Factor Reviews, 15, 255-273 (Year: 2004).*
Walter et al, Proc Am Thorac Soc, vol. 3, pp. 330-338 (Year: 2006).*
International Search Report for PCT/EP2014/051060, dated Mar. 19, 2014, 3 pages.
Written Opinion of the ISA for PCT/EP2014/051060, dated Mar. 19, 2014, 5 pages.

* cited by examiner

*Primary Examiner* — Sudhakar Katakam
(74) *Attorney, Agent, or Firm* — Nixon & Vanderhye P.C.

(57) ABSTRACT

The present invention relates to the use of compound 1-[4-methylthiophenyl]-3-[3,5-dimethyl-4-carboxydimethyl-methyloxyphenyl]prop-2-en-1-one for treating fibrotic diseases and cancers.

Figure 1:
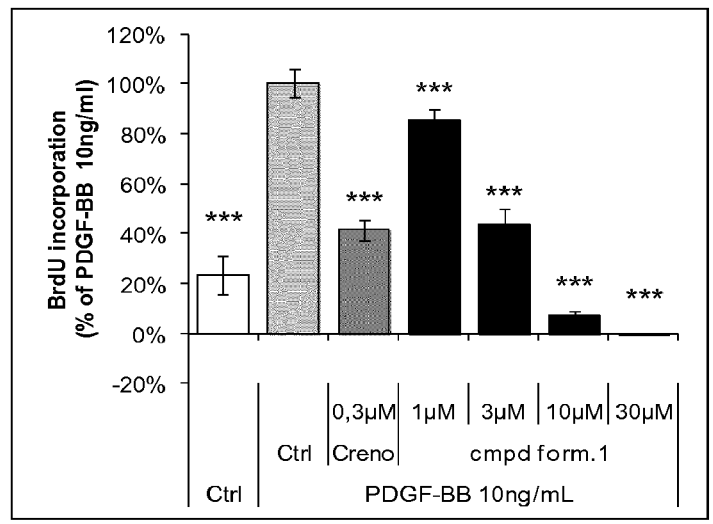

23 Claims, 3 Drawing Sheets
Specification includes a Sequence Listing.

METHODS OF TREATMENT OF FIBROSIS AND CANCERS

This application is a divisional of application Ser. No. 14/760,880 (pending), filed Jul. 14, 2015 (published as US 2015/0352065 A1), which is the U.S. national phase of International Application No. PCT/EP2014/051060 filed 20 Jan. 2014 which designated the U.S. and claims priority to EP Patent Application No. 13305067.4 filed 18 Jan. 2013, the entire contents of each of which are hereby incorporated by reference.

TECHNICAL HELD

The present invention relates to the use of compound 1-[4-methylthiophenyl]-3-[3,5-dimethyl-4-carboxydimethylmethyloxyphenyl]prop-2-en-1-one for treating fibrotic diseases and cancers.

BACKGROUND

Tyrosine kinases are important mediators of the signaling cascade, determining key roles in diverse biological processes like growth, differentiation, metabolism and apoptosis in response to external and internal stimuli. Recent advances have implicated the role of tyrosine kinases in the pathophysiology of fibrosis or cancers.

In regard to fibrosis, different tyrosine kinases have been identified as determinants of disease progression and potential targets for anti-fibrotic therapies. This includes both receptor tyrosine kinases (e.g., PDGF receptor, VEGF receptor, EGF receptor, and JAK kinases) as well as non-receptor tyrosine kinases (e.g., c-Abl, c-Kit, and Src kinases) [1]. In all fibrotic diseases, fibroblasts including stellate cells proliferate and are activated into myofibroblasts. Myofibroblasts are the principal collagen-producing cell type that undergoes hyperproliferation [2]. PDGFs are the primary mitogens for cells of mesenchymal origin. Excessive activity of PDGF has been associated with several human disorders, including organ fibrosis and tumorigenesis [3]. Elevated PDGF levels or activity has in particular been reported in pulmonary fibrosis, liver fibrosis [2], scleroderma [4-6], renal fibroproliferative diseases [7, 8], myeloproliferative diseases such as idiopathic myelofibrosis [9, 10], leukemia, in particular in leukemic cells of the bone marrow during progression of acute megakaryoblastic leukemia manifesting myelofibrosis [11] and chronic myelogenous leukemia [12-14].

Perhaps the most promising drugs for treating fibrosis are the PDGF receptor tyrosine kinase inhibitors. Administration of the PDGFR tyrosine kinase inhibitor has been shown to reduce pulmonary fibrosis in a rat model of metal-induced lung injury [15], and to ameliorate chronic allograft nephropathy in rats [16]. In patients with chronic myelogenous leukemia, a non selective PDGFR inhibitor, Imatinib (Gleevec) has been shown to induce regression of bone marrow fibrosis [17]. Taken together, these animal and preliminary clinical studies indicate that inhibition of PDGF receptor tyrosine kinases could offer a viable treatment strategy for fibrotic diseases in a variety of tissues.

In addition to agents that block the activity of the PDGFR pathway, both monoclonal antibodies and small-molecule inhibitors that block the aberrant activity of other tyrosine kinases were tested in preclinical models of various fibrotic diseases (e.g., idiopathic pulmonary fibrosis, renal fibrosis, liver fibrosis, and dermal fibrosis). The results of these studies were promising and prompted clinical trials with different compounds in fibrotic diseases. So far, results from studies with intedanib in idiopathic pulmonary fibrosis and imatinib in idiopathic pulmonary fibrosis and systemic sclerosis have been reported. Although none of these studies reported a positive primary outcome, promising trends in anti-fibrotic efficacy awaken our hopes for a new class of effective anti-fibrotic targeted therapies [1].

In regard to cancers, overexpression of growth factors and subsequent activation of specific receptor tyrosine kinases like PDGFRβ, VEGFRs can cause over-activation of the Raf/MEK/ERK mitogen-activated protein (MAP) kinase signaling pathway [18, 19]. Activation of the Raf/MEK/ERK mitogen-activated protein (MAP) kinase signaling pathway is known to increase cell proliferation and survival directly, and can indirectly stimulate angiogenesis by increasing the production of VEGF and PDGF [18]. These processes are required for tumor growth and, thus, the molecular components of the Raf/MEK/ERK signaling pathway are potential therapeutic targets for treating cancer, in particular for hepatocellular carcinoma (HCC) [20].

The anti-cancer drug Sorafenib inhibits the upstream receptor tyrosine kinases that are important in angiogenesis, including VEGFR-2, VEGFR-3, PDGFRβ, and kit and Raf serine/threonine kinase isoforrns (e.g. Raf-1 and B-Raf). Thus, Sorafenib can induce tumor cell death and inhibit angiogenesis. Sorafenib has also been shown to induce apoptosis in several tumor cell lines through mechanisms that are not well established [20, 21]. Sorafenib is the first FDA-approved systemic therapy for patients with advanced HCC not amenable to treatment by surgical resection or liver transplantation.

This altogether shows the interest of identifying new therapeutics acting on tyrosine kinases, for the treatment of fibrotic diseases or cancers.

SUMMARY OF INVENTION

The present invention provides novel uses of 1-[4-methylthiophenyl]-3-[3,5-dimethyl-4-carboxydimethylmethyloxyphenyl]prop-2-en-1-one in the preparation of pharmaceutical compositions for treating fibrotic diseases and cancers. 1-[4-Methylthiophenyl]-3-[3,5-dimethyl-4-carboxydimethylmethyloxyphenyl]prop-2-en-1-one has anti-fibrotic and anti-cancer properties through inhibition of receptor and non-receptor tyrosine kinases and/or inhibition of their intracellular signaling pathways in fibroblasts.

DESCRIPTION OF THE FIGURES AND TABLES

Abbreviations used in the figures, in the tables, and in the text:
Col1a1=collagen, type I, alpha 1
Col4a1=collagen, type 4, alpha 1
Cprn=counts per minute
Ctrl=control or vehicle
EGFR=Epidermal Growth Factor Receptor
ERK=Extracellular signal Regulated Kinase
FBS=fetal bovine serum
FCS=fetal calf serum
FDA=Food and Drug Administration
FGFR=Fibroblast Growth Factor Receptor
GIST=Gastrointestinal Stromal Tumor
HCC=Hepatocellular Carcinoma
HGFR=Hepatocyte Growth Factor Receptor
hHSC=human primary hepatic stellate
JAK=Janus Kinase
MAP=Mitogen-Activated Protein MEK=Mitogen-Activated Protein Kinase Kinase
PDGFR=Platelet-Derived Growth Factor Receptor
RCC=Renal Cell Carcinoma
RT-PCR=Reverse Transcription Polymerase Chain Reaction
TGFβR=Transforming Growth Factor beta Receptor
VEGFR=Vascular Endothelial Growth Factor Receptor FIG. 1. Compound of formula (I) interferes with hHSC cell proliferation that was induced by PDGF-BB The proliferation of human primary hepatic stellate cells (hHSC) was stimulated in vitro with PDGF-BB (10 ng/mL), which is the primary mitogen for mesenchymal cells. Crenolanib, a potent PDGFR inhibitor was used as a positive control. Crenolanib and the compound of formula (I) were added to the cell culture 1 hour before the stimulation with PDGF-BB in a serum free medium. Cell proliferation was assessed after 24 hours of incubation by measuring the incorporation of bromodeoxyuridine (BrdU).

Experimental results were expressed as mean±standard deviation (SD) and plotted as bar graphs. Statistical analyses were performed using an one-way ANOVA followed by Bonferroni post-hoc tests, using Sigma Plot 11.0 software.

[*: $p<0.05$; : $p<0.01$; *: $p<0.001$ (comparison versus PDGF-BB 10 ng/mL group)]

Figure 2:
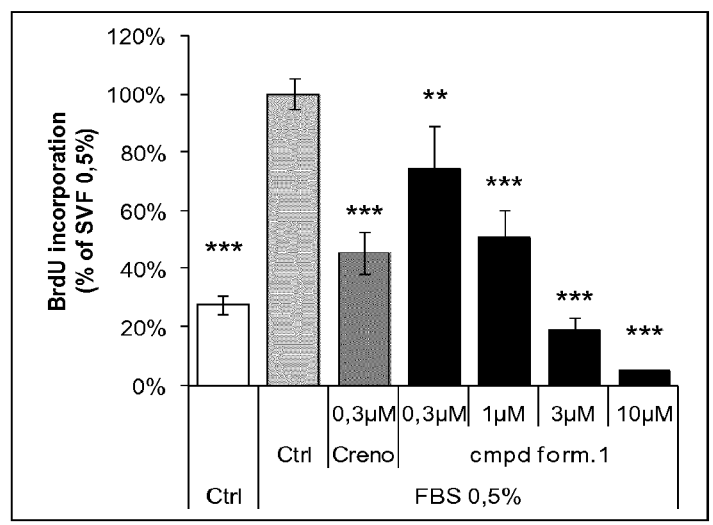

FIG. 2. Compound of formula (I) interferes with hHSC cell proliferation that was induced by serum The proliferation of human primary hepatic stellate cells (hHSC) was stimulated in vitro with fetal bovine serum, FBS (0.5%). Crenolanib, a potent PDGFR inhibitor was used as a positive control. Crenolanib and compound of formula (I) were added to the cell culture 1 hour before the stimulation with FBS. Cell proliferation was assessed after 48 hours of incubation by measuring the incorporation of bromodeoxyuridine (BrdU).

Experimental results were expressed as mean±standard deviation (SD) and plotted as bar graphs. Statistical analyses were performed using an one-way ANOVA followed by Bonferroni post-hoc tests, using Sigma Plot 11.0 software.

[*: $p<0.05$; : $p<0.01$; *: $p<0.001$ (comparison versus FBS 0.5% group)]

Figure 3:
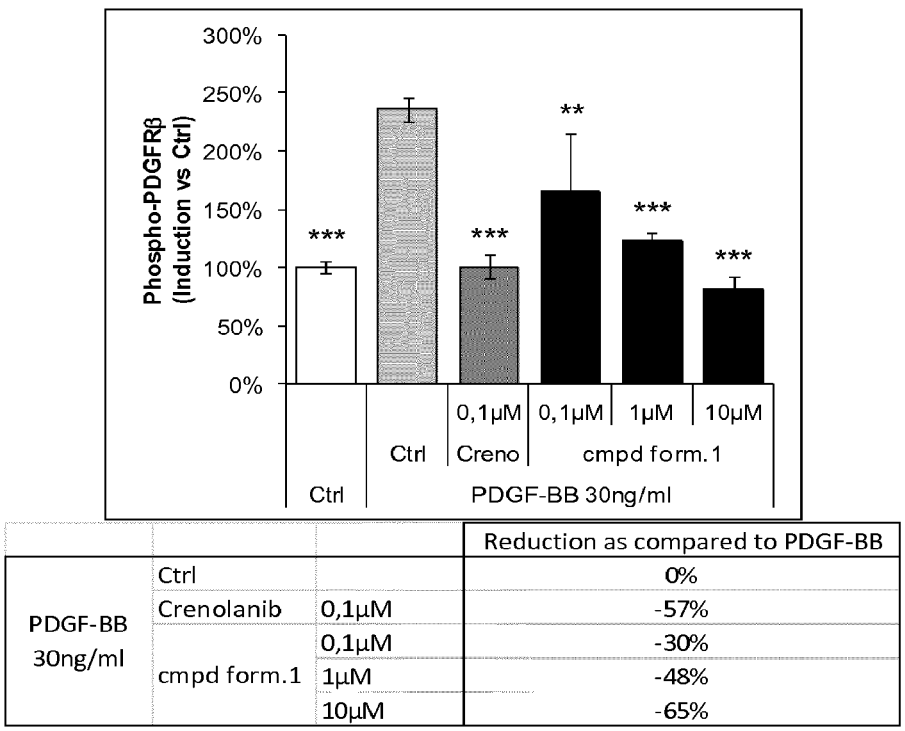

FIG. 3. Compound of formula I interferes with PDGF-BB induced PDGFRβ phosphorylation The phosphorylation of PDGFRβ was induced in hHSCs with PDGF-BB, in serum free conditions. The HSCs were first treated for 60 minutes with either Crenolanib (PDGFR inhibitor) or with compound of formula (I), then incubated for 10 minutes with PDGF-BB (30 ng/mL). The extent of the PDGFRβ phosphorylation on the tyrosine 751 was then determined by using the Human Phospho-PDGFRβ (Y751) Cell-Based ELISA kit (R&D Systems), upon fixation in culture wells.

Experimental results were expressed as mean±standard deviation (SD) and plotted as bar graphs. Statistical analyses were performed using an one-way ANOVA followed by Bonferroni post-hoc tests, using Sigma Plot 11.0 software.

[*: $p<0.05$; : $p<0.01$; *: $p<0.001$ (comparison versus PDGF-BB 30 ng/mL group)]

Figure 4:
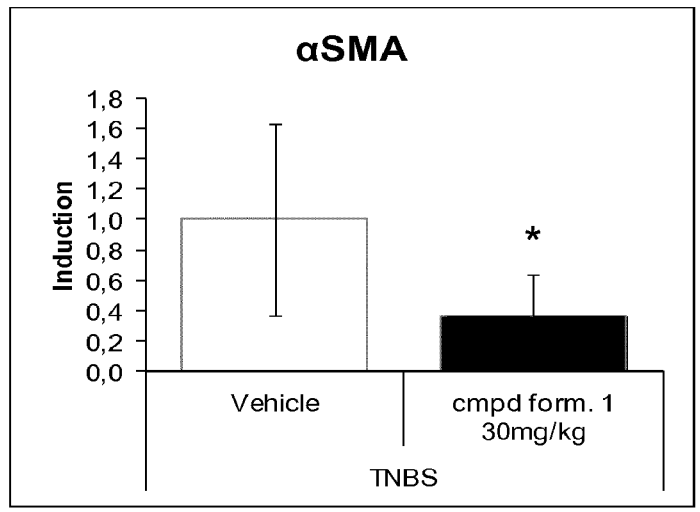

FIG. 4. Treatment with compound of formula (I) prevented the induction of colonic fibrosis in a model of inflammatory bowel disease.

The expression of α-SMA, a recognized biomarker of fibrotic response, in TNBS-induced colitis was partially prevented by the administration of compound of formula (I).

Experimental results were expressed as mean±standard deviation (SD) and plotted as bar graphs. Statistical analyses were performed using an t-test, [*: $p<0.05$]

Figure 5:
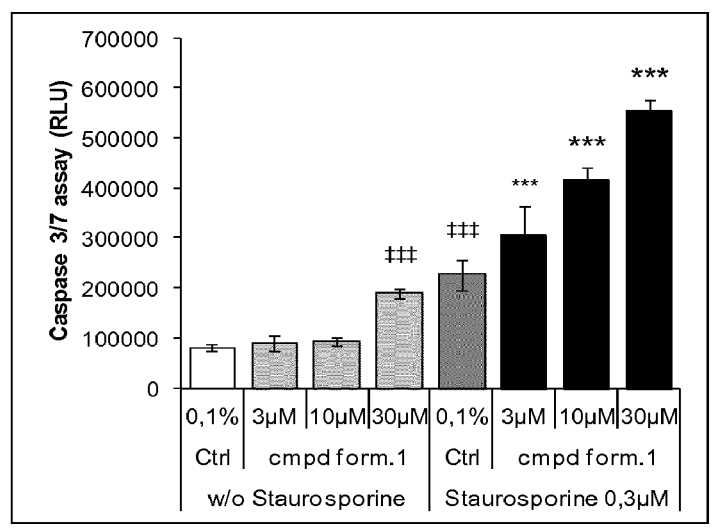

FIG. 5. Treatment with compound of formula (I) induced a modest proapoptotic response in activated hHSCs and significantly potentiated the proapoptotic effect of staurosporine Proapoptotic properties of compound of formula (I), either alone or in combination with Staurosporine, a broad spectrum protein kinase inhibitor, were assessed in the hHSC, HSCs were first exposed to serum deprivation for 16 hours and subsequently treated with either compound of formula (I) alone or with the combination of compound of formula (I) and staurosporine. The proapoptotic, effect of these treatments was assessed by using a Caspase-Glo® 3/7 activity assay kit.

Experimental results were expressed as mean±standard deviation (SD) and plotted as bar graphs. Statistical analyses were performed using an unpaired two-way ANOVA followed by Bonferroni post-hoc tests, using Sigma Plot 11.0 software.

[*: $p<0.05$; : $p<0.01$; *: $p<0.001$ (comparison versus "Staurosporine 0.3 μM" group)
‡: $p<0.05$; ‡‡: $p<0.01$ ‡‡‡: $p<0.001$ (comparison of the "w/o Staurosporine" group)]

DETAILED DESCRIPTION OF THE INVENTION

The present invention relates to the use of compound 1-[4-methylthiophenyl]-3-[3,5-dimethyl-4-carboxydimethylmethyloyphenyl]prop-2-en-1-one for treating fibrosis and cancers, such compound being capable of decreasing in an unexpected manner proliferation and activation of human fibroblasts including stellate cells, the main cellular type responsible for formation of extracellular matrix and fibrosis.

Compound 1-[4-methylthiophenyl]-3-[3,5-dimethyl-4-carboxydimethyln ethyl-oxyphenyl]prop-2-en-1-one to be used according to the invention has the following Formula (I):

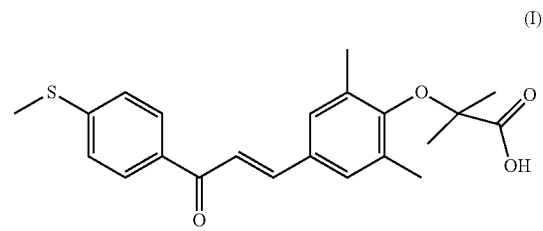 [SMILES: CSc1ccc(C(=O)/C=C/c2cc(C)c(OC(C)(C)C(=O)O)c(C)c2)cc1]

The prior art does not teach that anti-fibrotic or anti-cancer effects are associated to 1-[4-methylthiophenyl]-3-[3,5-dimethyl-4-carboxydimethylmethyloxyphenyl]prop-2-en-1-one due to direct and/or indirect inhibition of receptor tyrosine kinases.

Accordingly, the invention relates to compound 1-[4-methylthiophenyl]-3-[3,5-diethyl-4-carboxydimethylmethyloxyphenyl]prop-2-en-1-one for use in a method for the treatment or prevention of fibrotic diseases, wherein the fibrotic disease is not liver fibrosis, or for the treatment or prevention of a tyrosine kinase related cancer.

In a further aspect, the invention relates to the compound of Formula (I) for use in the inhibition of proliferation and/or activation of cells responsible for the production of collagen fibers and/or responsible for the production of the extracellular matrix.

The invention further relates to the compound of Formula (I) for use in promoting apoptosis of cells responsible for the production of collagen fibers and/or responsible for the production of the extracellular matrix.

According to the present invention, the term "fibrosis" includes in particular a lung, heart, muscle, skin, soft tissue (e.g mediastinum or retroperitoneum), bone marrow, intestinal, and joint (e.g. knee, shoulder or other joints) fibrosis. In particular, the term "fibrosis" includes, pulmonary fibrosis, idiopathic pulmonary fibrosis, cystic fibrosis, endomyocardial fibrosis, mediastinal fibrosis, myelofibrosis, retroperitoneal fibrosis, progressive massive fibrosis (a complication of coal workers' pneumoconiosis), nephrogenic systemic fibrosis, Crohn's disease, keloid, old myocardial infarction, scleroderma/systemic sclerosis, arthrofibrosis and some forms of adhesive capsulitis. The term "fibrosis" does not include liver fibrosis in the context of the present invention.

Receptor tyrosine kinases are widely abundant and dysregulated in cancers, and have been the focus of targeted therapies for several decades, using small molecules or antibodies [22-24].

TABLE 1

Selected examples of Receptor Tyrosine Kinase-targeted cancer therapies

| Type of cancer | Target | References |
|---|---|---|
| Breast cancer | HER2, EGFR, PDGFR, FGFR, IGFR, VEGFR, SRC | [25-28] |
| Chronic myeloid leukemia | BCR-ABL, SRC, TEC | [29-31] |
| Colorectal cancer | EGFR, VEGFR | [32-34] |
| Dermatofibrosarcoma | c-KIT, PDGFR, VEGFR | [35-38] |
| GIST | PDGFR, c-KIT, VEGFR, HER2 | [39-42] |
| Kidney cancer | VEGFR, PDGFR, c-KIT | [43-46] |
| Lung cancer | EGFR, VEGFR, ALK | [47-49] |
| Mastocytosis | BCR-ABL, PDGFR, c-KIT | [50-52] |
| Neurofibromatosis type 2 | PDGFR, EGFR, VEGFR | [53-57] |
| Pancreatic cancer | VEGFR, mTOR | [58, 59] |
| Prostate cancer | VEGFR, PDGFR, FGFR, EGFR, IGF1R | [28, 60] |
| Thyroid cancer | VEGFR, EGFR, c-met, RET | [61, 62] |

According to the present invention, the wording "tyrosine kinase-related cancer" means any form of cancer that relies on a deregulated activity or expression of a single or a group of tyrosine kinase receptors. In a particular embodiment of the invention, the tyrosine kinase is a receptor tyrosine kinase, more particularly PDGFR, VEGFR, FGFR, EGFR, c-Kit, or JAK kinases or non-receptor tyrosine kinases, more particularly c-Abl, or Src kinases. According to a particular embodiment, the term cancer includes hepatocellular carcinoma, renal cell carcinoma, gastrointestinal stromal tumor (GIST), gastric cancer, menigioma associated with neurofibromatosis, pancreatic neuroendocrine tumors, pancreatic exocrine tumors, leukemia, myeloproliferative/myelodisplastic diseases, mastocytosis, dermatofibrosarcoma, solid tumors including breast, lung, thyroid and colorectal cancers, prostate cancer In a particular aspect, the invention relates to the curative treatment of a liver cancer, in particular of a hepatocellular carcinoma.

In another aspect, the invention relates to the treatment or the prevention of a cancer different from a liver cancer. In particular, the cancer may be selected from renal cell carcinoma, gastrointestinal stromal tumor (GIST), menigioma associated with neurofibromatosis, pancreatic neuroendocrine tumors, pancreatic exocrine tumors leukemia, myeloproliferative/myelodisplastic diseases, mastocytosis, dermatofibrosarcoma, solid tumors including breast, lung, thyroid and colorectal cancers, prostate cancer. In a particular aspect, the prevented or treated cancer is a fibrotic cancer.

The treatment or prevention involves the administration of the compound or a pharmaceutical composition containing the same to a patient having a declared disorder to cure, delay, or slow down the progress, thus improving the condition of the patient or to a healthy subject, in particular a subject who is at risk of developing a fibrotic disease.

The subjects to be treated according to the invention can be selected on the basis of several criteria associated to fibrotic diseases or the cancers such as previous drug treatments, associated pathologies, genotype, exposure to risk factors, viral infection, as well as any other relevant biomarker that can be evaluated by means of imaging methods and immunological, biochemical, enzymatic, chemical, or nucleic acid detection method.

1-[4-methylthiophenyl]-3-[3,5-dimethyl-4-carboxydimethylethyloxyphenyl]prop-2-en-1-one can have different stable isomeric forms.

Synthesis of compound 1-[4-methylthiophenyl]-3-[3,5-dimethyl-4-carboxydimethylmethyloxyphenyl]prop-2-en-1-one can for example be carried out as described for compound 29 in WO2004/005233.

The compound of Formula (I) can be formulated as pharmaceutically acceptable salts, being slightly- or non-toxic salts obtained from organic or inorganic bases or acids of compound of Formula (I). These salts can be obtained during the final purification step of the compound or by incorporating the salt into the previously purified compound.

The pharmaceutical compositions comprising a compound of Formula (I) for the treatment of fibrotic diseases or cancers can comprise one or several excipients Or vehicles, acceptable within a pharmaceutical context (e.g. saline solutions, physiological solutions, isotonic solutions, etc., compatible with pharmaceutical usage and well-known by one of ordinary skill in the art). These compositions can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, carboxymethylcellulose, polysorbate 80, mannitol, gelatin, lactose, vegetable oils, acacia, liposomes, etc. These compositions can be formulated in the form of injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used.

The compound of Formula (I) may be administered in an efficient amount by using a pharmaceutical composition as above-defined. Within the context of the invention, the term "efficient amount" refers to an amount of the compound sufficient to produce the desired therapeutic result.

The compound of Formula (I) can be administered in different ways and in different forms. Thus, for example, it can be administered in a systematic way, per os, parenterally, by inhalation, or by injection, such as for example intravenously, by intra-muscular route, by subcutaneous route, by transdermal route, by intra-arterial route, etc. Oral administration is the preferential route of administration for pharmaceutical compositions comprising the compound of Formula (I).

The frequency and/or dose relative to the administration can be adapted by one of ordinary skill in the art, in function of the patient, the pathology, the form of administration, etc. Typically, the compounds of Formula (I) can be administered for the treatment of fibrotic diseases or cancers at doses varying between 0.01 mg and 1 g per administration, preferentially from 1 mg to 100 mg per administration. Administration can be performed daily or even several times per day, if necessary.

In a particular embodiment, the invention relates to the use of the compound of Formula (I) for the treatment of a fibrotic disease or cancer, in combination with at least one other therapeutically active agent. The other active agent may in particular be selected from other anti-fibrotic agents or other anti-cancer agents such as Sorafenib. The inventors have shown that the compound of Formula (I) is able to potentiate the pro apoptotic activity of a pro-apoptotic compound. Accordingly, the invention also relates to the use of the compound of Formula (I) in combination with a pro-apoptotic drug. In particular, the compound of Formula (I) may be used in combination with a kinase inhibitor having a pro-apoptotic effect on fibroblasts, such as Staurosporine.

In a further embodiment, the present invention provides methods of treating fibrotic diseases or cancers comprising the administration of the compound of Formula (I), in particular in the form of a pharmaceutical composition containing this compound.

The invention is further described with reference to the following, non-limiting, examples.

EXAMPLES

Materials & Methods

Compounds were dissolved in dimethyl sulfoxide (DMSO, Fluka cat #41640)

hHSC Culture and Treatment Conditions

The human primary hepatic stellate cells (hHSC) ScienCell) were cultured in STeCM medium (ScienCell cat #5301) that was supplemented with 2% fetal bovine serum (FBS, ScienCell cat #0010), 1% penicillin/streptomycine (ScienCell cat #0503) and stellate cell growth supplement (SteCGS; ScienCell cat #5352). Culture plastics were coated with Poly-L Lysine (Sigma cat # P4707). hHSC were plated at a density of $1.2 \times 10^4$ cells/well into 96-well plates and were cultured overnight at 37° C. and 5% $CO_2$, followed by washing of cells with PBS (Invitrogen cat #14190) and replacing the growth medium with a serum-free and SteCGS-free medium for an additional 24 hours.

For PDGF-induced proliferation assay, cells were pre-treated with all compounds for 1 hour before the addition of PDGF-BB (10 ng/mL; R&D Systems cat #520-BB). Treatments were then continued for an additional 20 hours. For serum induced proliferation assay, cells were pre-treated with compounds for 1 hour before FBS (0.5%) (ScienCell cat #0010) was applied in a SteCGS-free medium for 20 hours.

Determination of PDGF-Induced Proliferation

Cell proliferation was measured by bromodeoxyuridine (BrdU) incorporation using a BrdU labeling and detection kit (Roche cat #11647229001). BrdU labeling solution was added to cells, followed by incubation for another 4 hours before fixation, addition of nucleases, addition of anti-BrdU-POD and peroxidase substrate. The absorbance at 405 nm (with a reference wavelength at 690 nm) was measured using an ELISA plate reader (Tecan).

PDGF-Induced PDGFRβ Phosphorylation Assay

The PDGFR3 phosphorylation in hHSCs was measured using a cell based ELISA kit (R&D Systems cat # KCB1767), according to manufacturer's instructions. Shortly, following the stimulation with PDGF, cells were fixed and permeabilized in the wells. The PDGFRβ phosphorylation was then measured by using a double immunoenzymatic labeling procedure. The cells were simultaneously incubated with two primary antibodies: a phospho-specific antibody that detects the phosphorylation of the PDGFRβ on tyrosine 751 and a control antibody that recognizes both phosphorylated and non-phosphorylated forms of the PDGFRβ. Two secondary antibodies labeled with either horseradish-peroxidase (HRP) or alkaline phosphatase (AP), and two spectrally distinct fluorogenic substrates for either HRP or AP were used for detection. The fluorescence of the phosphorylated PDGFRβ was normalized to that of the pan-protein. The fluorescence was measured using an ELISA plate reader (Tecan).

HSC Activation with TGF-β1

The human primary hepatic stellate cells (hHSC) (ScienCell) were cultured under standard conditions, as described above. For experiments to determine gene expression patterns, hHSC were plated at a density of $1.4 \times 10^5$ cells/well into 12-well plates and were cultured overnight. Next day, culture medium was removed, cells were washed with PBS (Invitrogen cat #14190) and serum-free and SteCGS-free medium was added for an additional 16 hours. Cells were treated with compounds in addition to TGFβ1 (1 ng/mL) in a serum-free and SteCGS-free medium for 24 hours.

Gene Expression

Total RNA was isolated using RNeasy® Mini Kit (Qiagen) following manufacturer's instructions. 250 ng of total RNA were reverse transcribed in cDNA using M-MLV RT (Moloney Murine Leukemia Virus Reverse Transcriptase) (Invitrogen cat #28025) in presence of RT buffer 1× (Invitrogen), 1 mM DTT (Invitrogen), 0.18 mM dNTPs (Promega), 200 ng pdN6 (Amersham) and 30 U of RNase inhibitor (Promega).

Quantitative PCR was then carried out using the MyiQ Single-Color Real-Time PCR Detection or the iCycler iQ Multiplex Real-Time PCR Detection System (both systems from Biorad). Briefly, PCR reactions were performed in 96 Well plates on 5 µL of 5× diluted reverse transcription mix using the iQ SYBR Green Supermix kit. The experimental conditions were: 25 µL of volume reaction, 3 mM of $MgCl_2$, and 0.5 µL each of reverse and forward primers (10 pMol).

| Primer name | Sequence ID | Sequence (5'→3') |
|---|---|---|
| αSMA forward | 1 | ACTGCCTTGGTGTGTGACAA |
| αSMA reverse | 2 | TGGTGATGATGCCATGTTCT |
| Col1α1 forward | 3 | AATGGTGCTCCTGGTATTGC |
| Col1α1 reverse | 4 | ACCAGGTTCACCGCTGTTAC |
| Col4α1 forward | 5 | GTTGGTCTACCGGGACTCAA |
| Col4α1 reverse | 6 | GTTCACCTCTGATCCCCTGA |
| TGFβR1 forward | 7 | TGTTGGTACCCAAGGAAAGC |
| TGFβR1 reverse | 8 | CACTCTGTGGTTTGGAGCAA |
| VEGFR1 forward | 9 | TGTCAATGTGAAACCCCAGA |
| VEGFR1 reverse | 10 | GTCACACCTTGCTTCGGAAT |

-continued

| Primer name | Sequence ID | Sequence (5'→3') |
|---|---|---|
| VEGFR2 forward | 11 | AGCGATGGCCTCTTCTGTAA |
| VEGFR2 reverse | 12 | ACACGACTCCATGTTGGTCA |
| HGFR forward | 13 | CAGGCAGTGCAGCATGTAGT |
| HGFR reverse | 14 | GATGATTCCCTCGGTCAGAA |
| FGFR1 forward | 15 | GAAGTTCAAATGCCCTTCCA |
| FGFR1 reverse | 16 | CCAGCTGGTATGTGTGGTTG |
| c-KIT forward | 17 | GTCTCCACCATCCATCCATC |
| c-KIT reverse | 18 | GTTGGTGCACGTGTATTTGC |
| 36B4 forward | 19 | CATGCTCAACATCTCCCCTTCTCC |
| 36B4 reverse | 20 | GGGAAGGTGTAATCCGTCTCCACAG |

Expression levels were normalized using the expression of 36B4 gene as reference.

For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

The induction factor vs TGFβ1 was determined as follow:

$$\text{Induction factor} = \frac{A - B}{B}$$

With
A=expression level of the studied gene in the tested group
B=expression level of the studied gene in the TGFβ1 ng/mL group Thus, lower the induction factor is more the compound of interest inhibits the TGFβ1 activation of hHSC. Experimental results were expressed as mean±standard deviation (SD) of the induction factor.

Evaluation of Apoptosis by Measuring of Caspase 3/7 Activation

The human primary hepatic stellate cells (hHSC) (Scien-Cell) were cultured under standard conditions, as described above. For apoptosis assays, hHSC were plated at a density of $1.2 \times 10^4$ cells/well into black 96-well plates and were cultured for 24 hours at 37° C. and 5% $CO_2$, followed by washing of cells with PBS (Invitrogen cat #14190) and replacing the growth medium with a serum-Free and SteCGS-free medium for an additional 16 hours. Cells were treated with the compound of formula 1, either alone or in combination with staurosporine, in a serum-free and SteCGS-free medium for 24 hours. Caspase-3 and -7 activities were determined by using the assay from Promega (Promega cat # G8093) following manufacturer's instructions. At the end of the incubation period, 100 μL of Caspase-Glo® 3/7 Reagent were added to each well containing 100 μL of blank, negative control cells or treated cells in culture medium. Following cell lysis, the cleavage of the substrate (containing the DEVD sequence) by the activated caspases 3 and 7 was determined by measuring the luminescent signal in a classical plate reader from Tecan. Luminescence was proportional to the amount of caspase activity present in treated cells.

Measure of FGFR, PDGFR, VEGFR and c-Kit Protein Kinase Activity Inhibition

The kinase inhibition by the Compound of formula (I) was tested at 10 μM concentration on 10 selected kinases as presented in Table below. A radiometric protein kinase assay ($^{33}$PanQinase® Activity Assay) was used for measuring the kinase activity. The assay for all protein kinases contained 70 mM HEPES-NaOH pH 7.5, 3 mM $MgCl_2$, 3 mM $MnCl_2$, 3 μM Na-orthovanadate, 1.2 mM OTT, ATP (variable amounts, corresponding to the apparent ATP-Km of the respective kinase, see Table 1), [γ-$^{33}$P]-ATP (approx. $8 \times 10^5$ cpm per well), protein kinase (variable amounts, see Table 1), and substrate (variable amounts, see Table below).

Assay Parameters for the Tested Protein Kinases

| Kinase | Kinase Concentration (nM) | ATP Concentration (μM) | Substrate | Substrate Concentration (μg/50 μL) |
|---|---|---|---|---|
| FGFR1 | 10.4 | 3.0 | Poly(Glu, Tyr)4:1 | 0.125 |
| FGFR2 | 1.2 | 1.0 | Poly(Glu, Tyr)4:1 | 0.125 |
| FGFR3 | 13.5 | 3.0 | Poly(Glu, Tyr)4:1 | 0.250 |
| FGFR4 | 6.6 | 1.0 | Poly(Glu, Tyr)4:1 | 0.125 |
| c-KIT | 6.5 | 3.0 | Poly(Glu, Tyr)4:1 | 0.125 |
| PDGFRα | 22.2 | 10.0 | Poly(Ala, Glu, Lys, Tyr)6:2:5:1 | 0.125 |
| PDGFRβ | 4.5 | 0.3 | Poly(Ala, Glu, Lys, Tyr)6:2:5:1 | 0.125 |
| VEGFR1 | 4.5 | 1.0 | Poly(Glu, Tyr)4:1 | 0.125 |
| VEGFR2 | 5.7 | 1.0 | Poly(Glu, Tyr)4:1 | 0.125 |
| VEGFR3 | 4.7 | 3.0 | Poly(Glu, Tyr)4:1 | 0.125 |

The reaction cocktails were incubated at 30° C. for 60 minutes. The reaction was stopped with 50 μl of 2% (v/v) $H_3PO_4$, plates were aspirated and washed two times with 200 μL 0.9% (w/v) NaCl. Incorporation of $^{33}$P was determined with a microplate scintillation counter (Wicrobeta, Wallac).

For each kinase, the median value of the cpm of three wells with complete reaction cocktails, but without kinase, was defined as "low control". This value reflects unspecific binding of radioactivity to the plate in the absence of protein kinase but in the presence of the substrate. Additionally, for each kinase the median value of the cpm of three other wells with the complete reaction cocktail, but without any compound, was taken as the "high control", i.e. full activity in the absence of any inhibitor. The difference between high and low control was taken as 100% activity for each kinase.

As part of the data evaluation the low control value of each kinase was subtracted from the high control value as well as from their corresponding "compound values". The residual activity (in %) for each compound well was calculated by using the following formula:

Residual Activity (%) 100×[(cpm of compound−low control)/(high control−low control)].

Evaluation of the Inhibition of Human Tumor Cell Line Proliferation

This experiment demonstrated the direct inhibitory effects on cancer cell proliferation in vitro of the Compound of formula (I). 22 human tumor cell lines were cultured in complete media from ATCC containing 10% FBS at 37° C. in 5% $CO_2$ in an incubator. The cells in log-phase were used for proliferation assays. The cells were collected, counted, and then seeded at a suitable density in a 96-well plate and incubated for 16-24 hours. Then, various concentrations of the Compound of formula (I) were added (8 concentrations, 3 fold dilutions descending starting from 100 μM). Treatment medium was renewed every 24 hours during the 72 hour proliferation assay. The drug-treated cells and control cells were analyzed using the CellTiter-Glo® kit (Promega). Briefly, CellTite-Glo® Reagent were added to each test well and mixed for 2 minutes on an orbital shaker. The plates were shortly centrifuged at 90 g and incubated at room temperature for additional 10 minutes to stabilize the luminescent signal. Luminescence signals were on PHERAstar Plus.

Evaluation of Colon Wall Fibrosis Development in a Colitis Model

Compound of formula (I) was given orally at 30 mg/kg/day to the Sprague Dawley rats starting 5 days before the colitis induction by 2,4,6-trinitrobenzenesulfonic acid (TNBS) and until euthanasia.

For induction of colitis, the Sprague Dawley rats had been anesthetized for 2 hours using an intraperitoneal injection of pentobarbital. Colitis was induced by an intrarectal injection of TNBS (80 mg/kg in 40% Ethanol) at 8 cm from the anus. Animals were sacrificed 4 days after TNBS administration and the preventive effect of the Compound of formula (I) was assessed using gene expression assay.

α-SMA Gene Expression Studies in Colon Samples

Total RNA was isolated using RNeasy® Mini Kit (Qiagen) following manufacturer's instructions. 1 μg of total RNA were reverse transcribed in cDNA using M-MLV RT (Moloney Murine Leukemia Virus Reverse Transcriptase) (Invitrogen cat #28025) in presence of RT buffer 1× (Invitrogen), 1 mM DTT (Invitrogen), 0.18 mM dNTPs (Promega), 200 ng pdN6 (Amersham) and 30 U of RNase inhibitor (Promega). Quantitative PCR was then carried out using the CFX96 Touch™ Real-Time PCR Detection System (Biorad). Briefly, PCR reactions were performed in 96 well plates on 5 μL of 5× diluted reverse transcription mix using the iQ SYBR Green Supermix kit. The experimental conditions were: 25 μL of volume reaction, 3 mM of $MgCl_2$, and 0.5 μL each of reverse and forward primers (10 pMol).

| Primer name | Sequence (5'→3') |
| --- | --- |
| αSMA forward (SEQ ID NO: 1) | ACTGGGACGACATGGAAAAG |
| αSMA reverse (SEO ID NO: 2) | CATCTCCAGAGTCCAGCACA |

Expression levels were normalized using the expression of 36B4 gene as reference.

| Primer name | Sequence (5'→3') |
| --- | --- |
| 36B4 forward (SEQ ID NO: 19) | CATGCTCAACATCTCCCCCTTCTCC |
| 36B4 reverse (SEQ ID NO: 20) | GGGAAGGTGTAATCCGTCTCCACAG |

For each gene, the standard curves were drawn by selecting the best points (at least three points) in order to have PCR reaction efficiency close to 100% and a correlation coefficient close to 1. Expression levels were determined using the standard curve equation for both the housekeeping gene and the target gene (taking into account the specific PCR efficiency of each target gene).

The induction factor vs TNBS-treated rats was determined as follow:

$$\text{Induction factor} = \frac{A - B}{B}$$

With

A=expression level of the studied gene in the TNB+ Compound of the formula (I) at 30 mg/kg/day group B=expression level of the studied gene in the TNBS group Thus, lower the induction factor is more the compound of interest inhibits the TNBS-induced fibrosis of the colon wall. Experimental results were expressed as mean±standard deviation (SD) of the induction factor.

RESULTS & CONCLUSIONS

Excessive activity of PDGF has been associated with several human disorders, including organ fibrosis and tumorigenesis. PDGF plays a key role in expansion of myofibroblasts by stimulating their proliferation, migration and survival.

Unexpectedly, our experimental data showed that the compound of Formula (I) inhibits, in a dose-dependent way, the proliferation of hHSC that was induced either by a treatment with PDGF (FIG. 1) or by a treatment with serum (FIG. 2). As demonstrated on FIGS. 1 and 2, the efficacy of the compound of Formula (I) is comparable to that of a selective PDGFR inhibitor, Crenolanib. The compound of Formula (I) has anti-proliferative properties and interferes with the functional activation of the PDGFR signaling pathway Ligand-induced receptor homo- or heterodimerization leads to autophosphorylation of specific tyrosine residues within the cytoplasmic domain of PDGFR and to activation of some signal transduction pathways, including phosphatidylinositol 3 kinase (PI3K), Ras-MAPK, Src family kinases and phospholipase Cγ (PLCγ). This results in the stimulation of cell proliferation and survival.

Unexpectedly, our experimental data showed that the compound of Formula (I) inhibits, the phosphorylation of tyrosine 751 on the PDGFRβ that was induced in hHSC by the PDGF-BB, The inhibition by the compound of Formula (I) is dose-dependent and as efficacious as the inhibition obtained with a selective PDGFR inhibitor, Crenolanib (FIG. 3).

In regard to fibrosis, different receptor tyrosine kinases have been already identified as determinants of disease progression and potential targets for anti-fibrotic therapies. Recent preclinical results indicate that a simultaneous inhibition of PDGFR, VEGFR and FGFR activated pathways resulted in enhanced anti-fibrotic activity in pulmonary fibrosis models as compared to a treatment that inhibits the PDGFR pathway more selectively. As shown in Table 2, inventors have unexpectedly found that the compound of Formula (I) was able to inhibit the kinase activity of selected kinases, including the receptor tyrosine kinases PDGFR, VEGFR, FGFR that are involved in both fibrosis and cancer development.

TABLE 2

Compound of Formula (I) inhibits kinase activity of
selected receptor tyrosine kinases as measured in
a biochemical kinase activity assay. Reported results were
obtained at the concentration of 10 µmole/L.

|  | Inhibition rate (%) |
|---|---|
| FGFR1 | 20% |
| FGFR2 | 61% |
| FGFR3 | 42% |
| FGFR4 | 41% |
| VEGFR1 | 47% |
| VEGFR2 | 70% |
| VEGFR3 | 28% |
| c-KIT | 74% |
| PDGFRα | 4% |
| PDGFRβ | 61% |

As shown in Table 3, inventors have unexpectedly found that in addition to direct kinase inhibition properties, the compound of Formula (I) was able to inhibit, in activated hHSC, the expression of both classical pro-fibrotic genes, such as αSMA, Col1α1, Col4α1, TGFβR1, that are induced upon TGFβ31 treatment and the expression of VEGFR1, VEGFR2, FGFR1, tyrosine kinase receptors that are associated with the development of fibrosis as judged from the previously published sources [63]. As shown in Table 3, the gene inhibition profile of the compound of Formula (I) was very similar to that obtained with Sorafenib, a tyrosine kinase inhibitor that targets PDGFR, VEGFR, RAF and KIT. Sorafenib has previously demonstrated important anti-fibrotic activity in preclinical models and clinical efficacy in treatment of such cancers as hepatocellular carcinoma (HCC) and renal cell carcinoma (RCC) [64-66].

The expression of both profibrotic and cancer associated genes was induced in the primary human hepatic stellate cells (hHSCs) by the treatment with the TGFβ1 (1 ng/mL) in serum free conditions. Sorafenib (Nevaxar), a multiple receptor tyrosine kinase inhibitor that exerts both anti-fibrotic and anti-cancer properties, was used as a reference compound. The expression of the genes of interest in both treated and untreated hHSCs was determined by the quantitative RT-PCR technique, following 24 hours of exposure to the TGFβ1.

Experimental results were expressed as Emax values that indicate the maximum inhibition, which was obtained at the concentration of 10 µmole/L. Statistical analyses were performed using an one-way ANOVA followed by Bonferroni post-hoc tests, using Sigma Plot 11.0 software.

TABLE 3

Compound of Formula (I) and Sorafenib, both interfere with the
expression of the same target genes that were induced in hHSCs
by the treatment with the TGFβ1

| | Reduction in target gene expression as compared to hHSC cells treated with TGFβ1 (1 ng/mL) alone | | | | | |
|---|---|---|---|---|---|---|
| | Reduction induced by compound of formula 1 | | | Reduction induced by Sorafenib | | |
| Target gene | Conc. | Emax | p value | Conc. | Emax | p value |
| αSMA | 10 µM | −90% | *** | 10 µM | −95% | *** |
| Col1α1 | 10 µM | −56% | *** | 3 µM | −93% | *** |
| Col4α1 | 10 µM | −41% | ** | 10 µM | −93% | *** |
| TGFβR1 | 10 µM | −44% | ** | 10 µM | −80% | *** |
| VEGFR1 | 10 µM | −90% | *** | 10 µM | −95% | *** |
| VEGFR2 | 10 µM | −45% | * | 3 µM | −73% | *** |

TABLE 3-continued

Compound of Formula (I) and Sorafenib, both interfere with the
expression of the same target genes that were induced in hHSCs
by the treatment with the TGFβ1

| | Reduction in target gene expression as compared to hHSC cells treated with TGFβ1 (1 ng/mL) alone | | | | | |
|---|---|---|---|---|---|---|
| | Reduction induced by compound of formula 1 | | | Reduction induced by Sorafenib | | |
| Target gene | Conc. | Emax | p value | Conc. | Emax | p value |
| HGFR | 10 µM | −47% | * | 10 µM | −79% | *** |
| FGFR1 | 1 µM | −33% | * | 3 µM | −43% | ** |
| c-KIT | 10 µM | −98% | *** | ND | | |

[*: $p < 0.05$; : $p < 0.01$; *: $p < 0.001$ (comparison versus TGFβ1 1 ng/mL group)]

Intestinal fibrosis is a pathogenic feature of inflammatory bowel disease (IBD) [67] and is present in preclinical models of this disease. So far, no treatment was identified to either prevent fibrosis development in IBD or to treat the installed fibrosis. As shown in FIG. 4, inventors have unexpectedly found that colitis-induced increase in a fibrosis marker (α-SMA) expression in the colon was partially prevented by the compound of Formula (I) administration in 2,4,6-trinitrobenzenesulfonic acid (TNBS) induced preclinical model of IBD. This suggests that the compound of Formula (I) can prevent and/or treat fibrosis development in different organs and different disorders.

TABLE 4

Compound of Formula (I) inhibits the proliferation of experimental cell
lines derived from the selected types of cancer. Inhibition rates are
expressed as EC50 values in µmole/l that were calculated by curve
fitting of the experimental data as described in materials and methods.

| type of cancer | Tumor cell line | $EC_{50}$ (µM) |
|---|---|---|
| Renal cell carcinoma | 786-O | 28 |
| Meningioma associated with neurofibromatosis | T98G | 4 |
| | U-87 MG | 17 |
| Leukemia | CCRF-CEM | 2 |
| | MOLT-4 | ≥5 |
| Solid tumors in Non-small-cell lung cancer | A549 | ≥34 |
| | NCI-H460 | ≥29 |
| Solid tumors in colorectal cancer | SW480 | 3 |
| | Caco-2 | ≥43 |
| Gastrointestinal stromal tumor (GIST) | AGS | ≥27 |
| | MKN-45 | 11 |
| Pancreatic neuroendocrine tumor | BxPC-3 | 14 |
| | AsPc-1 | 16 |
| Myeloproliferative/myelodysplastic diseases | RPMI 8226 | 11 |
| Dermatofibrosarcoma | A431 | ≥31 |
| | A375 | ≥44 |
| Solid tumors in breast cancer | MDA-MB-468 | 22 |
| | MCF7 | 16 |
| Solid tumors in thyroid cancer | HTC-C3 | 6 |
| Prostate cancer | LNCaP | ≥14 |
| | PC-3 | 5 |

Most of the therapeutic compounds with anti-cancer activity interfere with cancerous cell proliferation. As shown in Table 4, inventors have unexpectedly found that compound of Formula (I) inhibited proliferation of diverse cancer cell-lines that correspond to different types of tumors.

The capacity to induce activated hHSC apoptosis is an important target in fibrotic diseases. The inventors have unexpectedly found that the compound of Formula (I) has modest pro-apoptotic properties, as shown in FIG. 5, but that it unexpectedly potentiated, in a dose-dependent manner, the pro-apoptotic activity of a broad spectrum kinase inhibitor, Staurosporine.

REFERENCES

1. Beyer, C., et al., Biochim Biophys Acta, 2012.
2. Bonner, W C., Cytokine Growth Factor Rev, 2004. 15(4): p. 255-73.
3. Alvarez, R. H., et al., Mayo Olin Proc, 2006. 81(9): p. 1241-57.
4. Klareskog, L., et al., Arthritis Rheum, 1990. 33(10): p. 1534-41.
5. Ludwicka, A., et al., J Rheumatol, 1995. 22(10): p. 1876-83.
6. Yamakage, A., et al., J Exp Med, 1992. 175(5): p. 1227-34.
7. Abboud, H. E., Annu Rev Physiol, 1995. 57: p. 297-309.
8. Alpers, C. E., et al., Kidney Int, 1992. 42(2): p. 390-9.
9. Caenazzo, A., et al., Acta Haematol, 1989. 81(3): p. 131-5.
10. Martyre, M. G., et al., Br J Haematol, 1991. 77(1): p. 80-6.
11. Kitagawa, M., et al., Hum Pathol, 1994. 25(7): p. 723-6.
12. Katoh, O., et al., Am J Hematol, 1990. 35(3): p. 145-50.
13. Kimura, A., et al., Leuk Lymphoma, 1995. 18(3-4): p. 237-42.
14. Wickenhauser, C., et al., Leukemia, 1995. 9(2): p. 310-5.
15. Rice, A. B., et al., Am J Pathol, 1999. 155(1): p. 213-21.
16. Savikko, J., et al., Transplantation, 2003. 75(8): p. 1147-53.
17. Beham-Schmid, C., et al., Blood, 2002. 99(1): p. 381-3.
18. Gollob, J. A., et al., Semin Oncol, 2006. 33(4): p. 392-406.
19. Stockl, L., et al., Oncogene, 2003. 22(17): p. 2604-10.
20. Wilhelm, S. M., et al., Cancer Res, 2004. 64(19): p. 7099-109.
21. Wilhelm, S. M., et al., Mol Cancer Ther, 2008. 7(10): p. 3129-40.
22. Yarden, Y., et al., Nat Rev Cancer, 2012. 12(8): p. 553-63.
23. Halper, J., Vet Pathol, 2010. 47(1): p. 77-97.
24. Sliwkowski, M. X., et al., Science, 2013. 341(6151): p. 1192-8.
25. Montero, J. C., et al., Clin Cancer Res, 2011. 17(17): p. 5546-52.
26. Fratto, M. E., et al., Olin Ter. 2010. 161(5): p. 475-82.
27. Malavaki, C. J., et al., FEBS J, 2013. 280(10): p. 2477-89.
28. Lemieux, S., et al., Anticancer Agents Med Chem, 2013. 13(5): p. 748-61.
29. Qiu, Z. Y., et al., Cancer Biol Ther. 2013. 15(3).
30. Cortes, J. E., et al., N Engl J Med, 2013. 369(19): p. 1783-96.
31. Rassi, F. E., et al., Pharmgenomics Pers Med, 2013. 6: p. 57-62.
32. Walker, A. S., et al., J Cancer, 2014. 5(1): p. 44-57.
33. McKeown, E., et al., J Cancer, 2014. 5(1): p. 31-43.
34. Hocking, C. M., et al., Therap Adv Gastroenterol, 2014. 7(1): p. 20-37.
35. Fields, R. C., et al., Ann Surg Oncol, 2011. 18(2): p. 328-36.
36. Kamar, F. G., et al., Clin Sarcoma Res, 2013. 3(1): p. 5.
37. Kerob, D., et al., Clin Cancer Res, 2010. 16(12): p. 3288-95.
38. Malhotra, B., et al., Curr Opin Oncol, 2012. 24(4): p. 419-24.
39. Doyle, L. A., et al., Histopathology, 2014. 64(1): p. 53-67.
40. Miettinen, M., et al., Gastroenterol Clin North Am, 2013. 42(2): p. 399-415.
41. Joensuu, H., et al., Lancet, 2013. 382(9896): p. 973-83.
42. Corless, C. L., Mod Pathol, 2014. 27 Suppl 1: p. S1-S16.
43. Hutson, T. E., et al., J Clin Oncol, 2013.
44. Domblides, C., et al., Expert Opin Emerg Drugs, 2013. 18(4): p. 495-511.
45. Hepgur, M., et al., Biologics, 2013. 7: p. 139-48.
46. Heudel, P., et al., Olin Pharmacol, 2012. 4: p. 65-70.
47. Binder, D., et al., Olin Med Insights Oncol, 2013. 7: p. 221-234.
48. Savas, P., et al., J Thorac Dis, 2013. 5(Suppl 5): p. S579-S592.
49. Zarogoulidis, K., et al., J Thorac Dis, 2013. 5(Suppl 4): p. S389-S396.
50. Manlu, C. M., et al., Rev Med Suisse, 2013. 9(368): p. 17-21.
51. Georgin-Lavialle, S., et al., Blood, 2013. 121(8): p. 1285-95.
52. Verstovsek, S., Eur J Haematol, 2013. 90(2): p. 89-98.
53. Evans, D. G., Orphanet J Rare Dis, 2009. 4: p. 16.
54. Evans, D. G., et al., Olin Cancer Res, 2009. 15(16): p. 5032-9.
55. Norden, A. D., et al., J Neurooncol, 2010. 96(2): p. 211-7.
56. Karajannis, M. A., et al., Neuro Oncol, 2012. 14(9): p. 1163-70.
57. Nunes, F. P., et al., PLoS One, 2013. 8(3): p. e59941.
58. Zhang, J., et al., J Natl Cancer Inst, 2013. 105(14): p. 1005-17.
59. Bishi, S., et al., Expert Opin Drug Metab Toxicol, 2013. 9(6): p. 777-88.
60. Heidegger, I., et al., J Steroid Biochem Mol Biol, 2013. 138: p. 248-56.
61. Haddad, R. I., J Natl Compr Canc Netw, 2013. 11(5 Suppl): p. 705-7.
62. Jin, J., et al., Curr Probl Surg, 2013. 50(6): p. 241-89.
63. Chaudhary, N. I., et al., Eur Respir J, 2007. 29(5): p. 976-85.
64. Hennenberg, M., et al., Lab Invest, 2011. 91(2): p. 241-51.
65. Wang, Y., et al., J Hepatol, 2010. 53(1): p. 132-44.
66. Xie, B., et al., Dig Dis Sci, 2012. 57(5): p. 1122-9.
67. Latella, G., et al., Eur Rev Med Pharmacol Sci, 2013 17(10): p. 1283-304.

We claim:

1. A method of treating a fibrotic disease in a person in need thereof, wherein the fibrotic disease is not liver fibrosis, said method comprising administering to the person an effective amount of a tyrosine kinase inhibitor, wherein the tyrosine kinase inhibitor is 1-[4-methylthiophenyl]-3-[3,5-dimethyl-4-carboxydimethylmethyloxyphenyl]prop-2-en-1-one or a pharmaceutically acceptable salt thereof.

2. The method of claim 1, wherein the fibrotic disease is lung fibrosis, heart fibrosis, skin fibrosis, bone marrow fibrosis, or intestinal fibrosis.

3. The method of claim 1, wherein the fibrotic disease is pulmonary fibrosis, idiopathic pulmonary fibrosis, myelofibrosis, Crohn's Disease, old myocardial infarction, or scleroderma/systemic sclerosis.

4. The method of claim 1 wherein the tyrosine kinase inhibitor is administered as a pharmaceutical composition comprising an excipient, dispersant, solubiliser, stabilizer and/or preservative.

5. The method of claim 1 wherein the tyrosine kinase inhibitor is administered orally or parenterally.

6. The method of claim 1 wherein the tyrosine kinase inhibitor is administered as an injectable suspension, a gel, an oil, a pill, a suppository, a powder, a gel cap, a capsule, or an aerosol.

7. The method of claim 1 wherein the tyrosine kinase inhibitor is administered as a prolonged release galenic form or a slow release galenic form.

8. The method of claim 1 wherein the tyrosine kinase inhibitor is administered with at least one other therapeutically active agent.

9. The method of claim 8 wherein the at least one other therapeutically active agent is an anti-fibrotic agent.

10. The method of claim 1 wherein the fibrotic disease of the person is cured or progress of the fibrotic disease of the person is delayed as a result of the treatment method.

11. A method of treating a fibrotic disease, wherein the fibrotic disease is not liver fibrosis, the method comprising administering to a person at risk of developing the fibrotic disease an effective amount of a tyrosine kinase inhibitor, wherein the tyrosine kinase inhibitor is 1-[4-methylthiophenyl]-3-[3,5-dimethyl-4-carboxydimethylmethyloxyphenyl]prop-2-en-1-one or a pharmaceutically acceptable salt thereof, wherein development of the fibrotic disease is delayed as a result of the treatment method.

12. The method of claim 11, wherein the fibrotic disease is lung fibrosis, heart fibrosis, skin fibrosis, bone marrow fibrosis, or intestinal fibrosis.

13. The method of claim 11, wherein the fibrotic disease is pulmonary fibrosis, idiopathic pulmonary fibrosis myelofibrosis, Crohn's Disease, old myocardial infarction, or scleroderma/systemic sclerosis.

14. The method of claim 11 wherein the tyrosine kinase inhibitor is administered as a pharmaceutical composition comprising an excipient, dispersant, solubiliser, stabiliser and/or preservative.

15. The method of claim 11 wherein the tyrosine kinase inhibitor is administered as an injectable suspension, a gel, an oil, a pill, a suppository, a powder, a gel cap, a capsule, or an aerosol.

16. The method of claim 11 wherein the tyrosine kinase inhibitor is administered as a prolonged release galenic form or a slow release galenic form.

17. The method of claim 11 wherein the tyrosine kinase inhibitor is administered with at least one other therapeutically active agent.

18. The method of claim 17 wherein the at least one other therapeutically active agent is an anti-fibrotic agent.

19. A method of treating a tyrosine kinase-related cancer in a person in need thereof, said method comprising administering to the person a tyrosine kinase inhibitor, wherein the tyrosine kinase inhibitor is 1-[4-methylthiophenyl]-3-[3,5-dimethyl-4-carboxydimethylmethyloxyphenyl]prop-2-en-1-one or a pharmaceutically acceptable salt thereof, wherein tyrosine kinase related-cancer is a renal cell carcinoma, a gastrointestinal stromal tumor (GIST), menigioma associated with neurofibromatosis, a pancreatic neuroendocrine tumor, leukemia, a myeloproliferative/myelodisplastic disease, dermatofibrosarcoma, breast cancer, lung cancer, thyroid cancer, colorectal cancer or prostate cancer.

20. A method of treating liver cancer in a person in need thereof, said method comprising administering to the person a tyrosine kinase inhibitor, wherein the tyrosine kinase inhibitor is 1-[4-methylthiophenyl]-3-[3,5-dimethyl-4-carboxydimethylmethyloxyphenyl]prop-2-en-1-one or a pharmaceutically acceptable salt thereof.

21. The method of claim 20 wherein the liver cancer is a hepatocellular carcinoma.

22. A method of inhibiting proliferation and/or activation of cells responsible for the production of collagen fibers and/or responsible for the productions of extracellular matrix comprising administering a composition comprising tyrosine kinase inhibitor, wherein the tyrosine kinase inhibitor is 1-[4-methylthiophenyl]-3-[3,5-dimethyl-4-carboxydimethylmethyloxyphenyl]prop-2-en-1-one and a pharmaceutically acceptable excipient or vehicle to a person in need of said inhibiting.

23. A method of promoting apoptosis of cells responsible for the production of collagen fibers and/or responsible for the production of the extracellular matrix comprising administering a composition comprising tyrosine kinase inhibitor, wherein the tyrosine kinase inhibitor is 1-[4-methylthiophenyl]-3-[3,5-dimethyl-4-carboxydimethylmethyloxyphenyl]prop-2-en-1-one and a pharmaceutically acceptable excipient or vehicle to a person in need of said inhibiting to a person in need of said promoting.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: artificial
<220> FEATURE:
<223> OTHER INFORMATION: primer
```

```
<400> SEQUENCE: 1
actgccttgg tgtgtgacaa                                              20

<210> SEQ ID NO 2
<211> LENGTH: 20
<212> TYPE: DNA
<213> ORGANISM: artificial
<220> FEATURE:
<223> OTHER INFORMATION: primer

<400> SEQUENCE: 2
tggtgatgat gccatgttct                                              20

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
aatggtgctc ctggtattgc                                              20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
accaggttca ccgctgttac                                              20

<210> SEQ ID NO 5
<211> LENGTH: 20
<212> TYPE: DNA
<213> ORGANISM: artificial
<220> FEATURE:
<223> OTHER INFORMATION: primer

<400> SEQUENCE: 5
gttggtctac cgggactcaa                                              20

<210> SEQ ID NO 6
<211> LENGTH: 20
<212> TYPE: DNA
<213> ORGANISM: artificial
<220> FEATURE:
<223> OTHER INFORMATION: primer

<400> SEQUENCE: 6
gttcacctct gatcccctga                                              20

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
tgttggtacc caaggaaagc                                              20

<210> SEQ ID NO 8
```

```
<211> LENGTH: 20
<212> TYPE: DNA
<213> ORGANISM: artificial
<220> FEATURE:
<223> OTHER INFORMATION: primer

<400> SEQUENCE: 8
cactctgtgg tttggagcaa                                               20

<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9
tgtcaatgtg aaacccaga                                                20

<210> SEQ ID NO 10
<211> LENGTH: 20
<212> TYPE: DNA
<213> ORGANISM: artificial
<220> FEATURE:
<223> OTHER INFORMATION: primer

<400> SEQUENCE: 10
gtcacacctt gcttcggaat                                               20

<210> SEQ ID NO 11
<211> LENGTH: 20
<212> TYPE: DNA
<213> ORGANISM: artificial
<220> FEATURE:
<223> OTHER INFORMATION: primer

<400> SEQUENCE: 11
agcgatggcc tcttctgtaa                                               20

<210> SEQ ID NO 12
<211> LENGTH: 20
<212> TYPE: DNA
<213> ORGANISM: artificial
<220> FEATURE:
<223> OTHER INFORMATION: primer

<400> SEQUENCE: 12
acacgactcc atgttggtca                                               20

<210> SEQ ID NO 13
<211> LENGTH: 20
<212> TYPE: DNA
<213> ORGANISM: artificial
<220> FEATURE:
<223> OTHER INFORMATION: primer

<400> SEQUENCE: 13
caggcagtgc agcatgtagt                                               20

<210> SEQ ID NO 14
<211> LENGTH: 20
<212> TYPE: DNA
<213> ORGANISM: artificial
<220> FEATURE:
<223> OTHER INFORMATION: primer

<400> SEQUENCE: 14
```

```
gatgattccc tcggtcagaa                                                   20

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
gaagttcaaa tgcccttcca                                                   20

<210> SEQ ID NO 16
<211> LENGTH: 20
<212> TYPE: DNA
<213> ORGANISM: artificial
<220> FEATURE:
<223> OTHER INFORMATION: primer

<400> SEQUENCE: 16
ccagctggta tgtgtggttg                                                   20

<210> SEQ ID NO 17
<211> LENGTH: 20
<212> TYPE: DNA
<213> ORGANISM: artificial
<220> FEATURE:
<223> OTHER INFORMATION: primer

<400> SEQUENCE: 17
gtctccacca tccatccatc                                                   20

<210> SEQ ID NO 18
<211> LENGTH: 20
<212> TYPE: DNA
<213> ORGANISM: artificial
<220> FEATURE:
<223> OTHER INFORMATION: primer

<400> SEQUENCE: 18
gttggtgcac gtgtatttgc                                                   20

<210> SEQ ID NO 19
<211> LENGTH: 25
<212> TYPE: DNA
<213> ORGANISM: artificial
<220> FEATURE:
<223> OTHER INFORMATION: primer

<400> SEQUENCE: 19
catgctcaac atctccccct tctcc                                             25

<210> SEQ ID NO 20
<211> LENGTH: 25
<212> TYPE: DNA
<213> ORGANISM: artificial
<220> FEATURE:
<223> OTHER INFORMATION: primer

<400> SEQUENCE: 20
gggaaggtgt aatccgtctc cacag                                             25
```